(12) United States Patent
Cooper et al.

(10) Patent No.: US 10,123,739 B2
(45) Date of Patent: Nov. 13, 2018

(54) SUBJECT MOTION MONITORING, TEMPERATURE MONITORING, DATA GATHERING AND ANALYTICS SYSTEM AND METHOD

(71) Applicant: MONDEVICES INC., North Bergen, NJ (US)

(72) Inventors: Benjamin Cooper, Hingham, MA (US); Jeffrey Tagen, North Kingstown, RI (US)

(73) Assignee: MONDEVICES INC., North Bergen, NJ (US)

( * ) Notice: Subject to any disclaimer, the term of this patent is extended or adjusted under 35 U.S.C. 154(b) by 6 days.

(21) Appl. No.: 14/640,964

(22) Filed: Mar. 6, 2015

(65) Prior Publication Data
US 2015/0250419 A1 Sep. 10, 2015

Related U.S. Application Data

(60) Provisional application No. 61/949,546, filed on Mar. 7, 2014.

(51) Int. Cl.
*A61B 5/01* (2006.01)
*A61B 5/00* (2006.01)
(Continued)

(52) U.S. Cl.
CPC .......... *A61B 5/6804* (2013.01); *A61B 5/0002* (2013.01); *A61B 5/01* (2013.01);
(Continued)

(58) Field of Classification Search
CPC ....... A61B 5/6804; A61B 5/0002; A61B 5/11; A61B 5/113; A61B 5/01;
(Continued)

(56) References Cited

U.S. PATENT DOCUMENTS 5,684,460 A * 11/1997 Scanlon ................. A61B 5/113
340/573.1
6,409,654 B1 6/2002 McClain
(Continued)

FOREIGN PATENT DOCUMENTS

WO WO2013/093686 6/2013
WO WO2014/035836 3/2014

OTHER PUBLICATIONS

International Search Report and Written Opinion for International Application No. PCT/US2015/019263, dated Jun. 9, 2015. (8 pages).

*Primary Examiner* — Rex R Holmes
(74) *Attorney, Agent, or Firm* — Tutunjian & Bitetto, P.C.

(57) ABSTRACT

The monitoring device provides value to parents by assisting with monitoring their infants via a convenient sensor package, straightforward interface, and informative data. With movement, orientation, and temperature data, some strong indicators of general well-being can be monitored and conclusions extracted without the parent needing to be constantly involved. The low-power transceiver technology also means that the device can integrate with smart devices for even more convenience. Such a smart device can in turn communicate with modem large-scale data storage and analysis centers for data logging and analytics, which allows useful analytics to be passed back to the user. The advanced sensing, displaying, and analyzing of data makes the invention stands out in the field of infant monitoring devices.

4 Claims, 11 Drawing Sheets

(51) Int. Cl.
- *A61B 5/113* (2006.01)
- *G01G 19/50* (2006.01)
- *G01G 3/12* (2006.01)
- *G01G 5/00* (2006.01)
- *G01G 19/56* (2006.01)
- *G06F 19/00* (2018.01)
- *G16H 15/00* (2018.01)
- *A61B 5/11* (2006.01)
- *A61M 21/02* (2006.01)

(52) U.S. Cl.
CPC ............ *A61B 5/11* (2013.01); *A61B 5/113* (2013.01); *G01G 3/12* (2013.01); *G01G 5/00* (2013.01); *G01G 19/50* (2013.01); *G01G 19/56* (2013.01); *G06F 19/3418* (2013.01); *G16H 15/00* (2018.01); *A61B 5/0008* (2013.01); *A61B 5/1113* (2013.01); *A61B 5/4806* (2013.01); *A61B 5/746* (2013.01); *A61B 2503/04* (2013.01); *A61B 2503/06* (2013.01); *A61B 2503/08* (2013.01); *A61B 2560/0214* (2013.01); *A61B 2560/0242* (2013.01); *A61B 2560/0412* (2013.01); *A61B 2562/0219* (2013.01); *A61M 21/02* (2013.01); *A61M 2205/332* (2013.01); *A61M 2205/3303* (2013.01); *A61M 2205/3368* (2013.01); *A61M 2205/3375* (2013.01); *A61M 2205/3569* (2013.01); *A61M 2205/3592* (2013.01); *A61M 2205/50* (2013.01); *A61M 2205/502* (2013.01); *A61M 2205/8206* (2013.01); *A61M 2230/42* (2013.01); *A61M 2230/63* (2013.01); *A61M 2240/00* (2013.01)

(58) Field of Classification Search
CPC ........ A61B 2560/0242; A61B 2503/06; G06F 19/3487; G06F 19/3418; G01G 19/56; G01G 3/12; G01G 5/00; G01G 19/50; A61M 2205/3592

See application file for complete search history.

(56) References Cited

U.S. PATENT DOCUMENTS

| | | | |
|---|---|---|---|
| 2008/0262381 A1 | 10/2008 | Kolen | |
| 2010/0286545 A1* | 11/2010 | Wolfe | G06F 19/3418 600/534 |
| 2013/0116514 A1* | 5/2013 | Kroner | A61B 7/00 600/301 |
| 2013/0274587 A1* | 10/2013 | Coza | A61B 5/6804 600/409 |

\* cited by examiner

SUBJECT MOTION MONITORING, TEMPERATURE MONITORING, DATA GATHERING AND ANALYTICS SYSTEM AND METHOD

CROSS REFERENCE TO RELATED APPLICATIONS

This application claims priority from U.S. Provisional Application Ser. No. 61/949,546 filed on Mar. 7, 2014.

BACKGROUND

1. Field of the Invention

The present principles relate generally to infant and child safety and development systems, and more particularly to the technical field of monitoring systems.

2. Discussion of Related Art

Being a parent involves numerous worries about the health and safety of one's infant, toddler or child, including, for example, determining whether a sleeping infant is breathing. Infant monitoring devices can help alleviate some of parent's fears in the face of such worries, but many of these existing monitoring devices do not provide enough or the correct type of data for the parent. Audio and video monitors are a popular monitoring solution, but they require the parent to be actively monitoring the data stream and to be able to recognize potential issues by themselves only given that data feed. Furthermore, pressure pads put under the infant's mattress can detect the orientation of the infant, which has been linked to several problems (such as Sudden Infant Death Syndrome), but such devices can be fairly inaccurate, give off false positives, and are rendered useless if the baby move off the pad. One monitoring device currently found on the market does monitor motion of the infant, however it is bulky, prone to falling off, and has a very short battery life that frequently requires recharging. In addition to all of these shortcomings, such devices can cost upwards of several hundred dollars.

Presently there are no commercially available devices that provide detailed data on an infant, and thusly there are also no devices or services that can use such data to provide analytical data.

DETAILED DESCRIPTION

A monitoring system and method are provided that is capable of monitoring a subject, such as an infant, toddler, child, a disabled person or an elderly person and analyzing that data.

More specifically, the system has a device that gathers data from an infant, reports that data to a user-facing application for immediate data interpretation, and logs more data to a back-end system for further analytical analysis. The system may have a device being used (hereafter referred to as "the device") detects when it is in motion, its orientation, and the ambient temperature of its location and analyzes that data. The device may be secured to a subject such as an infant, toddler, child, disabled person or elderly person such that healthy movements (such as breathing, activity level, wakefulness, crying etc.) may be detected without bringing harm to the subject. The device may then communicate data gathered from the motion, orientation, and temperature detection systems to a separate device that does an initial interpretation of the data for the user. With this data, the immediate status of the infant to which the device is secured can be determined (such as whether the infant is breathing, its approximate temperature, temperature of the room, orientation of infant, etc). The data is also logged to a back-end system, which can do a more detailed analysis based off of aggregate data to offer advice and predictions for specific infants.

The system may include several components that work together to achieve numerous benefits, including low power consumption on the device and rapid warning of an alert condition. The device may have a number of features including movement detection from breathing detection, simple orientation detection, temperature sensing, the ability to transmit and receive data wirelessly, a processor to take care of gathering raw sensor data and transmitting a message using the wireless communication, a battery to provide power, and the packaging of these components. The system may also have a user-facing application run on a computing device, such as a smart device or provided hardware, which provides immediate interpretation of the data collection by the device to the user so that they can take any appropriate action. The system also may have a back-end system that retrieves and stores data from the user-facing application, using it to make assumptions and predictions for things not directly measured.

Figure 1:
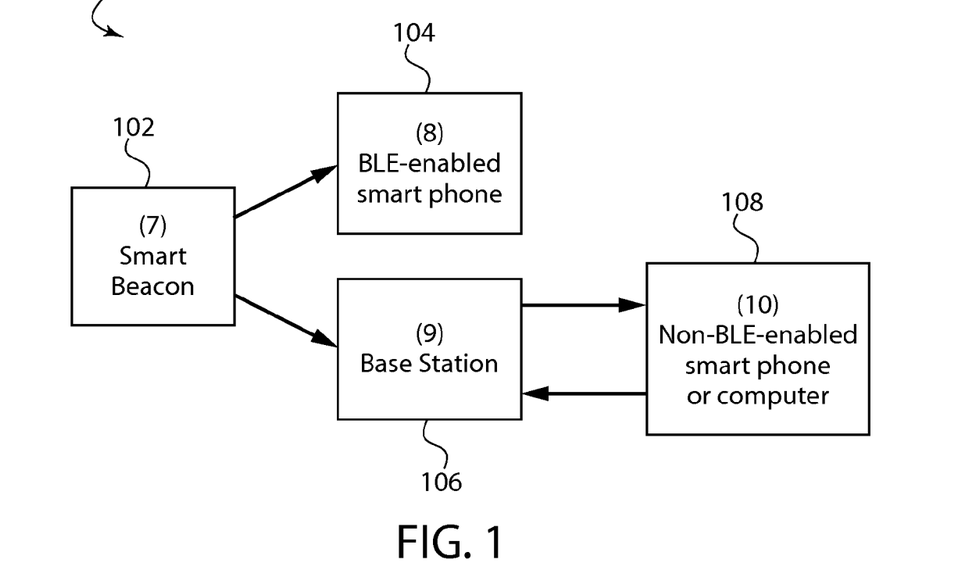
FIG. 1 shows an illustrative diagrammatic view of an implementation of a monitoring system that incorporates a monitoring device in accordance with an embodiment of the present invention.

FIG. 1 illustrates an implementation of a monitoring system 100 that incorporates a monitoring device 102, known as a smart beacon that may be attached to an infant piece of clothing and be worn while the infant is sleeping. The Smart Beacon 102 may be constantly sending data (using either broadcast protocols or a dedicated negotiated connection) data via a low-energy communications protocol (e.g., a low-energy RF communications protocol such as a Bluetooth enabled communications protocol) to either a computing device 104 or a dedicated base station 106. The computing device 104 (or base station) may be a processor based device with memory, circuits that allow the computing device to communicate wirelessly with the smart beacon 102 or base station 106 and a display. For example, the computing device 104 may be a smartphone device, a tablet computer device, a personal computer, a cellular phone device with sufficient display capabilities to interface with the smart beacon 102 or base station 106 and the like. The computing device 104 may display alerts or activate audible alarms about the infant and information related to performance of the smart beacon. The base station 106 can communicate with other devices, including laptops, desktops, tablets, and smartphones that do not support the low-energy RF wireless mechanism over a WiFi connection or other wireless or wired connection. In this case the base station acts as both an end access point for notifications as well as a relay to other devices 108. Additionally, the data may be transmitted to a back-end system (11) that stores previous data from the sensor as well as data from other sensors to be used as data for predictions regarding specific infants.

Figure 2:
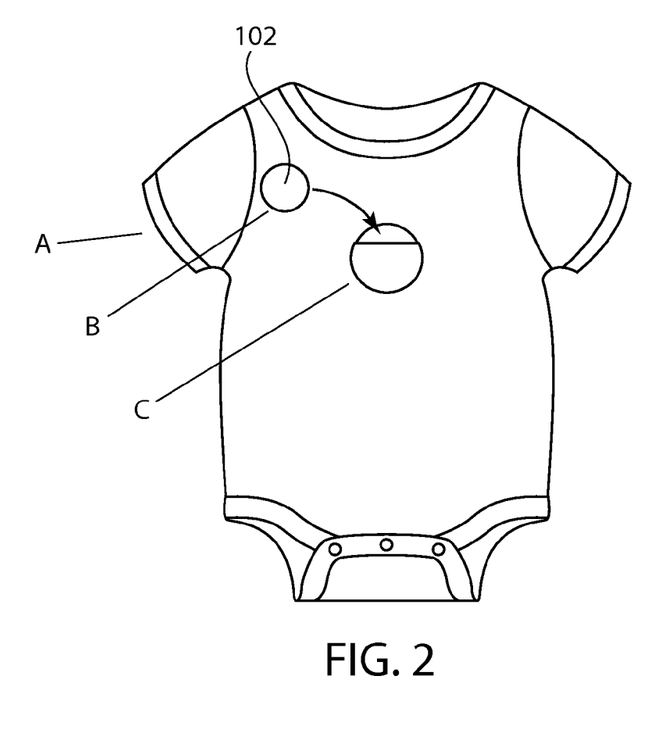
FIG. 2 shows an illustrative diagrammatic view of an example of an infant piece of clothing having a pocket for receiving monitoring device in accordance with an embodiment of the present invention.

FIG. 2 illustrates an example of an infant piece of clothing (A) having a monitoring device 102 in which the device 102 may be coupled to an infant's piece of clothing during operation. In one embodiment, the garment (A) may have a pocket (C) large enough to hold the entire device 102. The pocket is designed to permit the caregiver easy access to the device without an infant being able to access the device, and may have a high degree of pocket overlap of a top flap over the main panel. In certain embodiments, the device may be permitted a certain range of movement within the pocket. The pocket may be secured through various means, such as with the use of hook and loop fasteners, elastic stitching, fixed stitching, magnetic attachment or a button clasp. The pocket may be located on the chest of the garment so that the device may register movement from respiration. Using a pocket design allows the device to be easily removed by a parent when the garment needs to be washed, but is secure enough that the infant cannot remove the device themselves. In alternate embodiments, the device may be mounted to the piece of clothing using other mechanisms.

Figure 3:
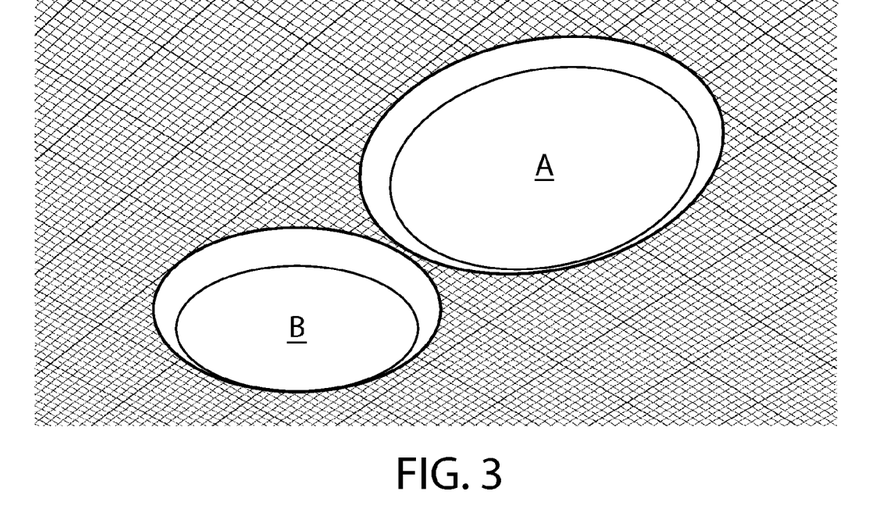
FIG. 3 shows illustrative diagrammatic views of a set of casings of the monitoring device in accordance with an embodiment of the present invention.
Figure 4:
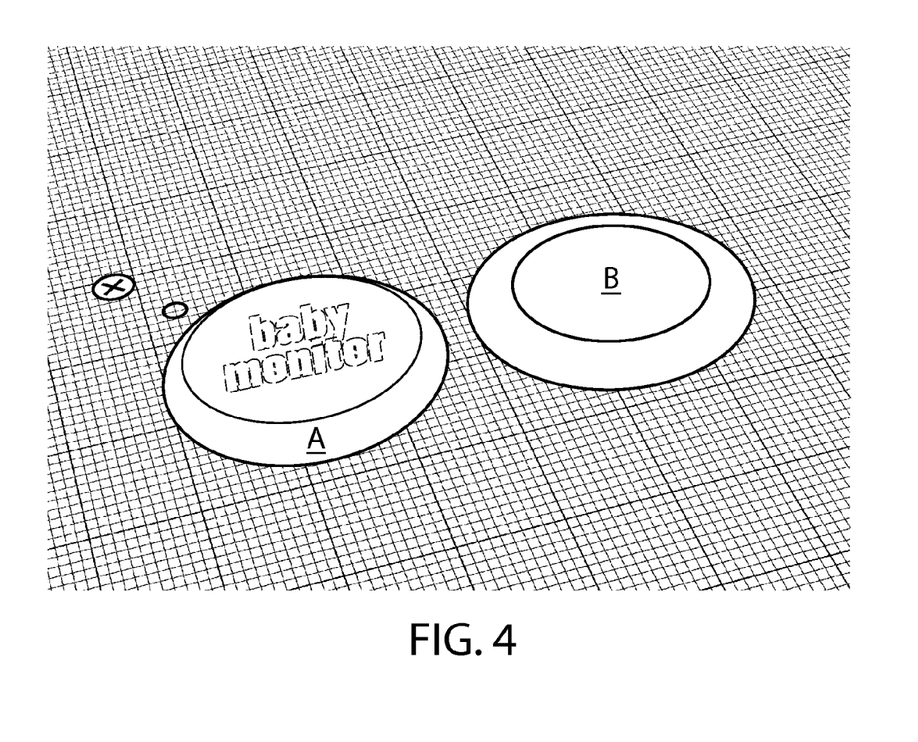
FIG. 4 shows illustrative diagrammatic views of outer surfaces of the set of casings of the monitoring device of FIG. 3.

FIG. 3 illustrates an example of a set of casings of the monitoring device 102. The monitoring device 102 may have a circular hollow design that allows the electronics to be stored inside the unit, while grooved edges allow parts A and B to be secured together either via some mechanical latching interface, or with an adhesive. The design is circular to prevent sharp edges, and fits within the size regulations for devices that interact with children. FIG. 4 illustrates an example of an outer surface of the set of casings of the monitoring device 102 in which the outside of each component may indicate the orientation in which the sensor should be placed. For example, an outer surface of part B indicates that it should be towards the baby, leaving an outer surface of part A to show a logo (as seen in FIG. 4) or other information.

Figure 5:
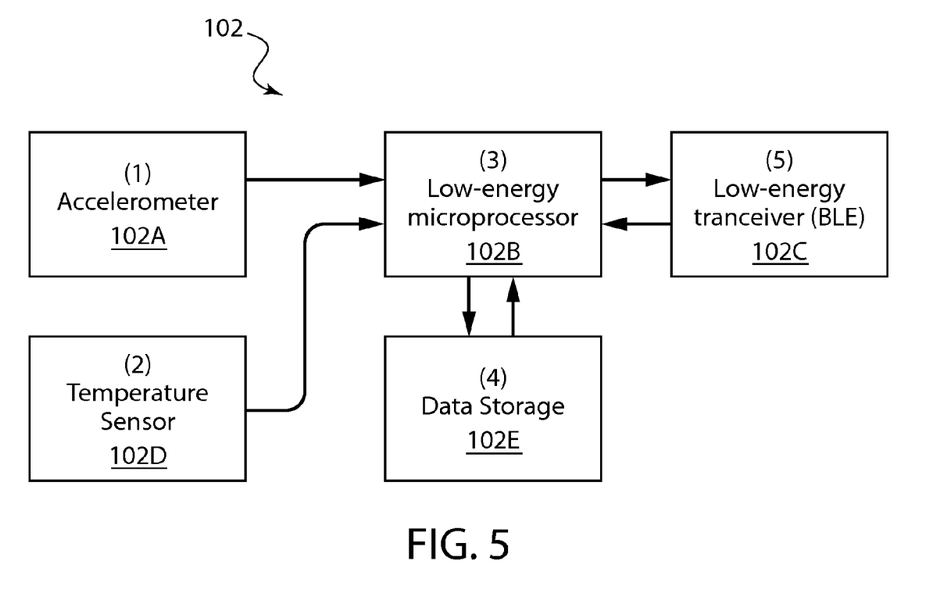
FIG. 5 shows illustrative diagrammatic functional views of a monitoring system in accordance with an embodiment of the present invention.

FIG. 5 illustrates an implementation of a beacon component 102 of the monitoring system in Figure I. The Smart Beacon 102 may contain both a thermocouple or thermistor based temperature sensor 102 D designed to operate efficiently in the 0-100 degree Celsius range, as well as an accelerometer 102A designed to measure acceleration in both the I-Gravity and microgravity ranges in up to three axes. The accelerometer component may also include rotation and magnetic sensors to determine orientation and movement (a 9-axis positioning/movement sensor). This data may be fed into a low-energy microprocessor 102B which has the capability of aggregating the data and sending it to the low-energy transceiver 102C, such as a typical lower power Bluetooth transceiver. The settings, preferences and data caching can be handled by an attached data storage device 102E. Not shown in this diagram are the required antenna, power source, and optional power regulation electronics which are included in the circuits in FIG. 5.

The smart beacon 102 may perform movements from breathing detection, simple orientation detection, temperature sensing, the ability to transmit and receive data wirelessly, a processor to take care of gathering raw sensor data and transmitting a message using the wireless communication, a battery to provide power, and the packaging of these components.

The movements from breathing detection may be detected with the use of an accelerometer 102A, that may be for example a three axis accelerometer, sensitive enough to register the acceleration caused by the rising and falling of an infant's chest when breathing. With the accelerometer mounted, for example, on the infant's chest, and with one axis pointing directly away from the infant (the z-axis), the majority of chest rising and falling due to breathing will be on this z-axis, minimizing the likelihood of the sensor missing the movement from breathing. When the chest rises to intake air, acceleration is seen, and when the chest falls to expel air, an opposite acceleration is seen. In this way, the accelerometer can measure the rise and fall of an infant's chest when properly aligned, which is a strong indicator that the infant is breathing.

The simple orientation detection is achieved using the accelerometer 102A used for movements from breathing detection. Simple orientation detection here simply means that the device can detect if an infant is lying on its back or on its chest. The z-axis of the accelerometer is on the infant's chest pointing away, meaning that at rest the device should approximately measure the pull of gravity at any given time (minus some noise for acceleration due to movements caused by breathing). This negative acceleration on the z-axis indicates that the infant is lying on their back. However, if the infant turns over to lie on their chest, the z-axis will now measure the acceleration of gravity as a positive number. Using this information, the Accelerometer can be used to determine the simple orientation of the infant.

The temperature sensing may be done using a thermistor or thermocouple 102D, a device. that changes resistance based on temperature. Using a thermistor within a voltage divider circuit allows the temperature to be represented as an analog voltage signal, so that as temperature increases or decreases, so will the voltage. The exact relationship between the temperature and the voltage is a factor of the circuit components and the properties of the thermistor. As long as the readings are sensitive enough to capture the difference between a healthy ambient temperature for an infant and an unhealthy ambient temperature for an infant, and thermistor will work. A thermocouple would work by measuring the change in current, which indicates a change in temperature (the relationship of which is again based on the particular sensor.)

The ability to transmit and receive data wirelessly can be achieved using vanous technologies, including Bluetooth, Wi-Fi, near-field communication, RFID, or some similar wireless protocol is currently achieved using a Bluetooth Low Energy module 102C. Such a module would ideally have low power consumption, meaning the device will be able to operate for longer periods of time without requiring recharging or new batteries. Such a module would also has have a fair transmission range; meaning that any capable device within an average-sized house can receive the data is transmits. In this way, the device can communicate with any other device that used Bluetooth Low Energy compatible with that communication mechanism/protocol within the average household, and doing so does not severely shorten battery life of the device overall compared to other wireless transmission methods.

The processor 102B that manages all of this data only needs to have 4 analog ports for the accelerometer inputs and the one temperature sensor input, and several digital pins to communicate with the wireless transceiver module. In terms of speed, the processor only needs to collect data from the two aforementioned sensors and transmit it at a rate of 1 Hz. The processor is also very low power, and is capable of going into a low power state when not gathering and transmitting data, prolonging the battery life of the device.

The battery used in the device is a small battery capable of fitting into the casing or within a modified package. Due to the low power consumption of all the electronic components, the battery should be able to provide sufficient power to all components for several months Before being replaced or recharged. As described above, the components may be packaged in a small disk-shaped plastic casing that may be large enough to meet size requirements for products in reach of infants, small enough to comfortably fit in a front pocket on an infant's night time attire, and is rounded to prevent possible injury due to sharp edges. The electronic components and battery for the device may be mounted onto a small circuit board, which is then placed within the plastic casing by sealing the two halves of the disk together with an adhesive. At this stage, all of the components within the device are receiving power, and the device is ready to transmit and receive data.

Figure 6:
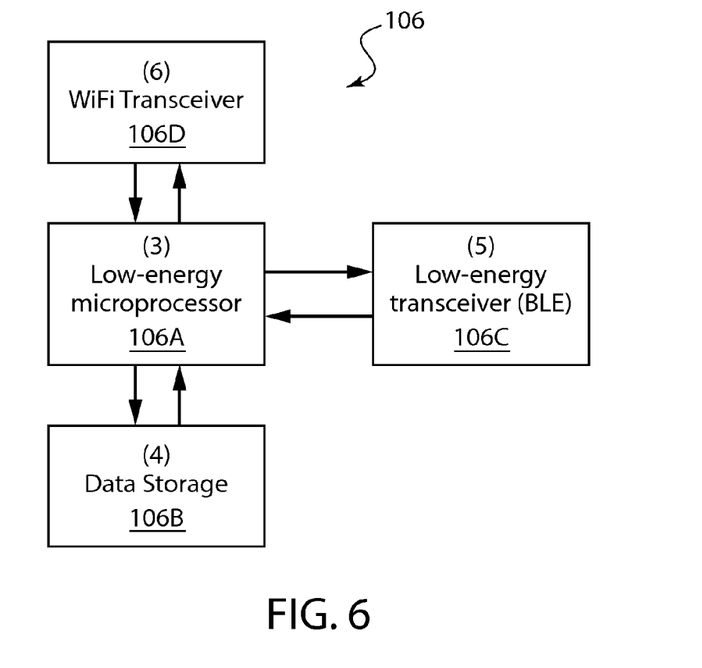
FIG. 6 shows an illustrative diagrammatic view of a base station component of a monitoring system in accordance with an embodiment of the present invention.

FIG. 6 illustrates an implementation of the base station 106 components of the monitoring system in FIG. 1. The base station components may include a same or similar low-energy microprocessor 106A, a transceiver 106C and a data storage device 106B as the beacon. The base station (again, which may be any of a desktop computer, a laptop computer, a tablet computer, a computer pad or a personal communication device such as a smart phone) is designed to gather and process data from the beacon and provide summary information either directly to the user or to relay the information through a wifi-connected 106D device. The system may also employ Internet access to provide a cloud communication network, for example, if a smart phone is used as the base station and communicates with one or more other smart phones. Not shown are components of the base station such as user input/output devices, including buttons, speakers, LCD displays, and other controls necessary to specify options and preferences related to the data received from the beacon. For example, a caregiver may provide to the system input data such as set sensitivity threshold, the subject's age, weight, a schedule of the subject feeding etc. The sensitivity threshold may set a low threshold (other than zero) below which an alarm is triggered.

Figure 7:
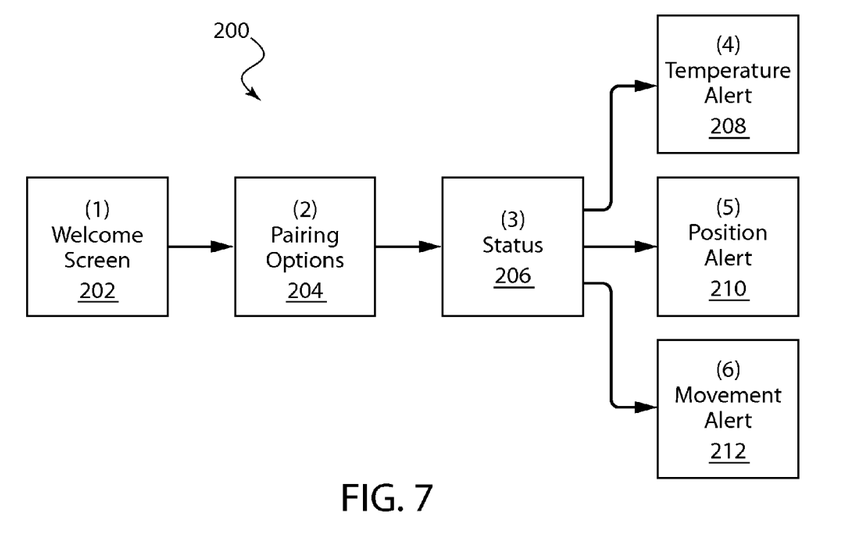
FIG. 7 shows an illustrative diagrammatic view of a flow of functional steps In a monitoring system in accordance with an embodiment of the present invention.

FIG. 7 illustrates a set of application functionality 200 of the monitoring system. The applications, including desktop, laptop, tablet, and smart-phone (both direct-lo-beacon and via base station) are designed to receive, interpret, and display data from the beacon. The application may be viewed using a typical browser application or the application may be an application resident on the computing device. The application functionality may include a welcome screen 202 with instructions, logos, and any required disclaimers. The user may be forwarded to a pairing screen 204 in which the app polls for nearby beacons and displays a list of available beacons to form a connection with or to start subscribing to broadcasts from. Once a beacon is selected, data is streamed to one or more status screens 206 that may continuously display processed data received from the beacon. The processed data may include biometric data, such as temperature and respiration rate, device data, such as battery level and signal strength, or historical data and other alerts. If an abnormal condition is detected, the app may alert the user through audio, visual, or tactical feedback mechanisms. This may include an alert of high or low temperature of the subject 208 or rapid changing of the ambient temperature, that the subject is sleeping in a non-optimal position 210, or that motion data 212 is not being adequately detected from the subject. Other alerts mechanisms and triggers may also be included with the application functionality.

The data going to the user-facing side of the invention is immediately used to display data on movement from breathing, orientation, and temperature gathered by the device. The data is displayed in an easily understood format, and can trigger an alert if the data seem abnormal. An alert indicates to the user if one of the measured statistics is out of the ordinary.

The back-end system takes all of the immediate data that is sent by the device and stores it for analysis. This can be done by communicating with a computer, either wirelessly or via a physical wire connection. Additional data can also be stored beyond what is measured by the device, through prompting the user for additional input in areas such as when the infant eats, sleeps, is active, a diaper is changed etc. The back-end can then take the data for a particular infant, along with data for many other infants, and analyze it for trends. Such analysis can yield information that a parent might find useful, such as predictive indicators. One example might be indicating when a given infant will be likely to sleep next, or when the infant will be hungry again. The data from an individual infant can also be compared against an aggregate of similar infants to deduce additional information, such as the presence of an abnormal sleep cycle.

Figure 8A:
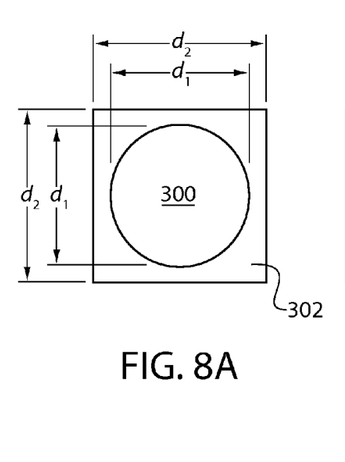
FIGS. 8A-8C show illustrative diagrammatic views of a motion sensor device of the present invention within a pocket on an article of clothing in accordance with an embodiment of the present invention.
Figure 8B:
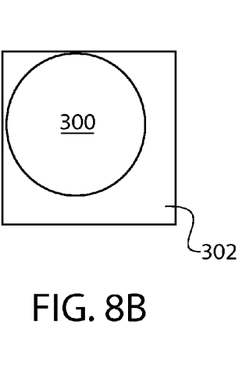
Figure 8C:
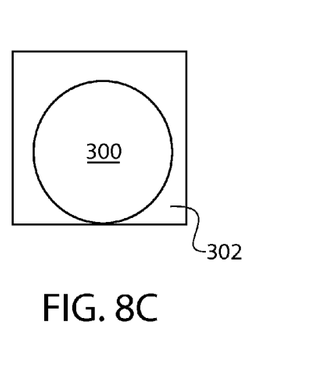

FIGS. 8A-8C show that a sensor device 300 may have a size (e.g., diameter d1) that is sufficiently smaller than the size of the pocket 302 (distance d2 by distance d2) such that the device 300 may be permitted to move around within the pocket. This is a sharp departure from known applications that employ accelerometers. In accordance with certain embodiments of the present invention, any movement of the accelerometer that is due to movement of the subject is acceptable, as it is the occurrence of no movement that is being monitored. The sensor device 300 (which includes the motion sensor) may be permitted to have a freedom of movement with respect to the pocket (and the subject) of at least 1 em. This permits the sensor device to be easily inserted and removed from the garment by parents without requiring complex or bulky attachment mechanisms.

Figure 9:
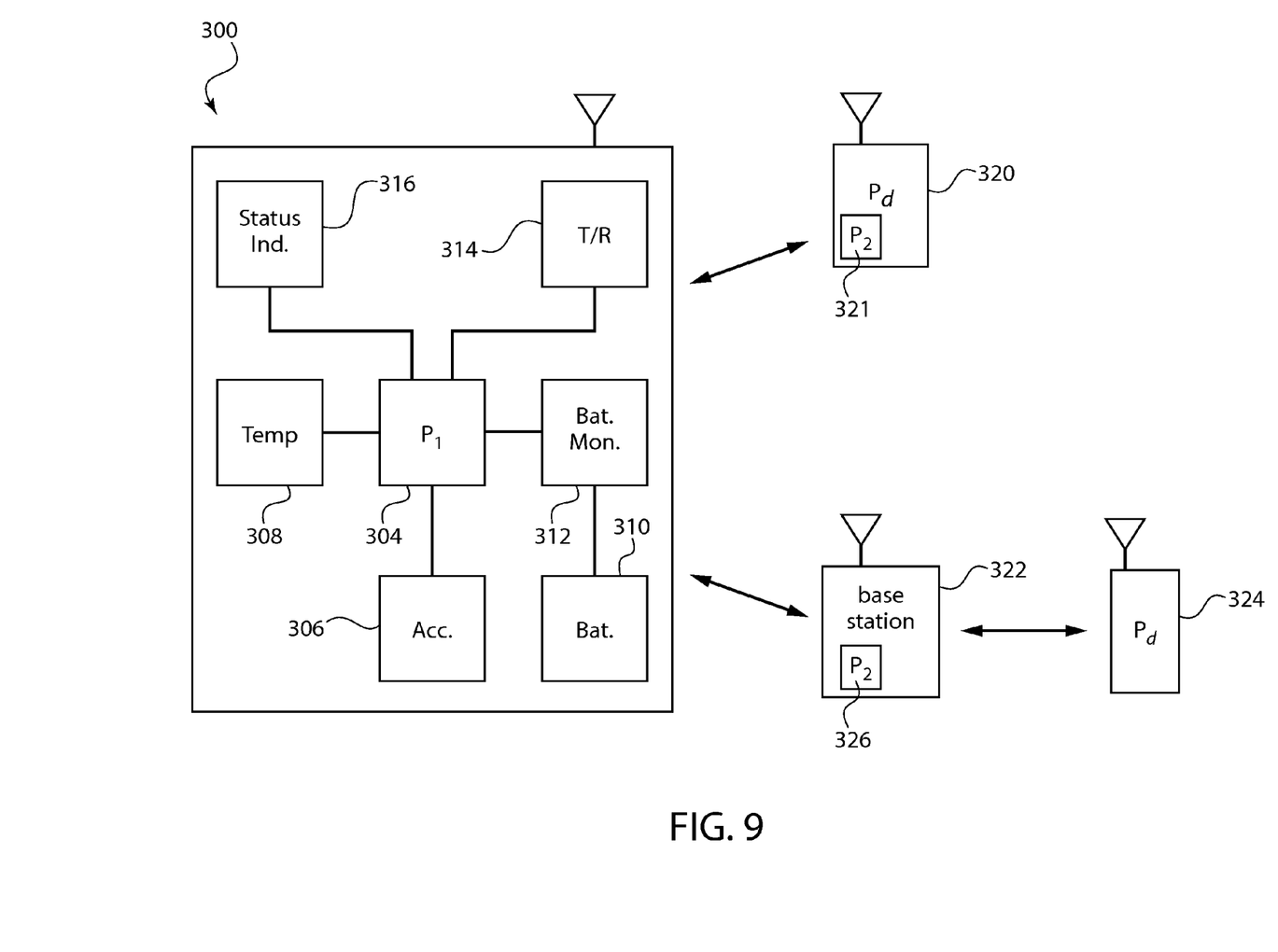
FIG. 9 shows an illustrative diagrammatic view of a monitoring system in accordance with an embodiment of the invention that may include a base station.

As shown in FIG. 9, a system in accordance with an embodiment of the invention may include a sensor device 300 that includes a first processor 304 (P1), an accelerometer such as a three axis MEMS accelerometer, a temperature sensor 308, a battery 310 and a battery status monitor 312. The device 300 also includes a transmit I receive circuit that communicates wirelessly to either a personal communication device 320 such as a smart phone, or to a base station 322 that in turn communicates with a personal communication device 324. The device 300 also includes a status indicator 316 that not only indicates the status of the device as being active, but also shows confirmation that the communication system with either personal communication devices 320, 324 and/or base station 322 are functioning properly. In accordance with further embodiments, the base station itself may be a personal communication device that relays information to another personal communication device.

Figure 10:
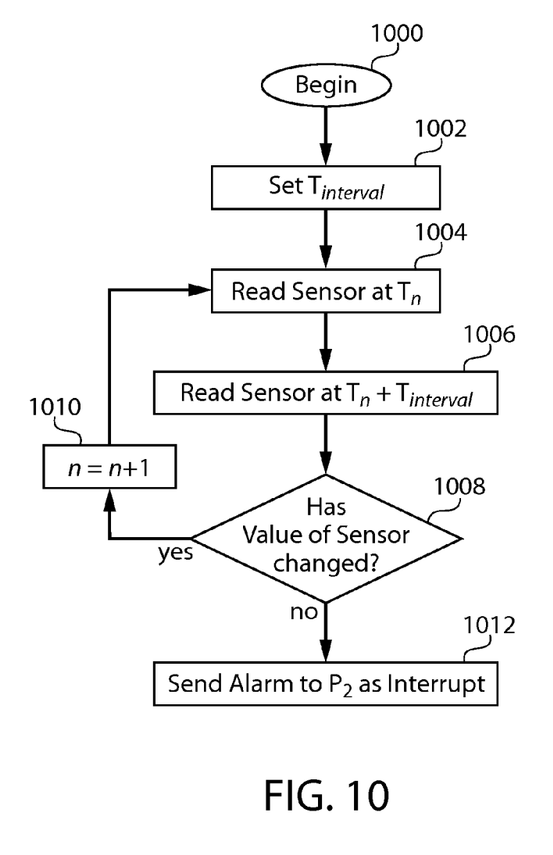
FIG. 10 shows an illustrative set of processing steps for a first processor in a system in accordance with an embodiment of the invention.

A first processor 304 is therefore running concurrently with either a processor (P2) in the personal communication device 320 as shown at 321 or a processor (P2) 306 in the base station 322. As shown in FIG. 10, in accordance with an embodiment, the first processor P1 may begin (step 1000) by setting a time interval Tinterval (step 1002) over which a change will be continuously monitored (e.g., 1 sec.). The motion sensor is then read at time Tn (step 1004) and then read again at time Tn+Tinterval (step 1006). The system may then determine whether the output of the motion sensor changed during that interval (step 1008), and if so, the clock time counter advances (step 1010) and the system returns to the step of reading the motion sensor (step 1004). If the output of the motion sensor has not changed during the interval (step 1008), the system sends an alarm condition signal to the processor P2 as an interrupt signal (step 1012).

Figure 11:
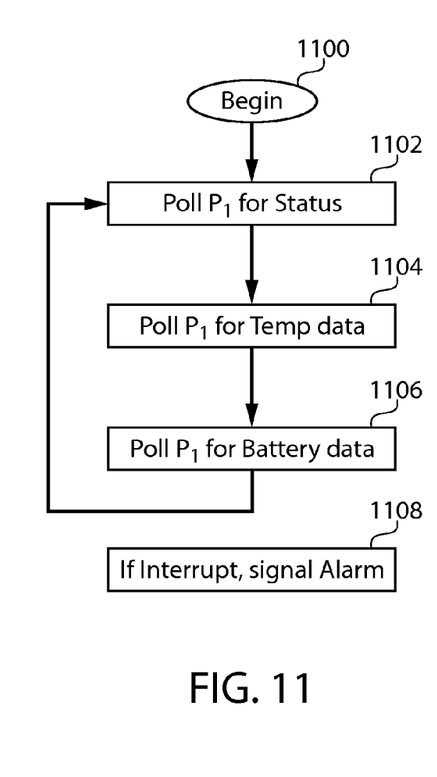
FIG. 11 shows an illustrative set of processing steps for a second processor in a system in accordance with an embodiment of the invention.

The second processor P2 of either the personal communication device 320 or the base station 326 may begin (1100) by polling P1 for the status of the device 300 as well as the status of the communication system between the components (step 1102). The system then polls P1 for measured temperature data from the temperature sensor 308 on the device (step 1104). Then the system polls P1 for battery status data from the battery monitor 312 on the device (step 1106). If an interrupt is encountered at any time, the system sends an alarm signal directly to the personal communication device 320, 324 (step 1108). The processor P 1 pushed the data therefore to the processor 2 responsive to the detection that the motion has not changed or has not changed above a set threshold of movement.

Figure 12:
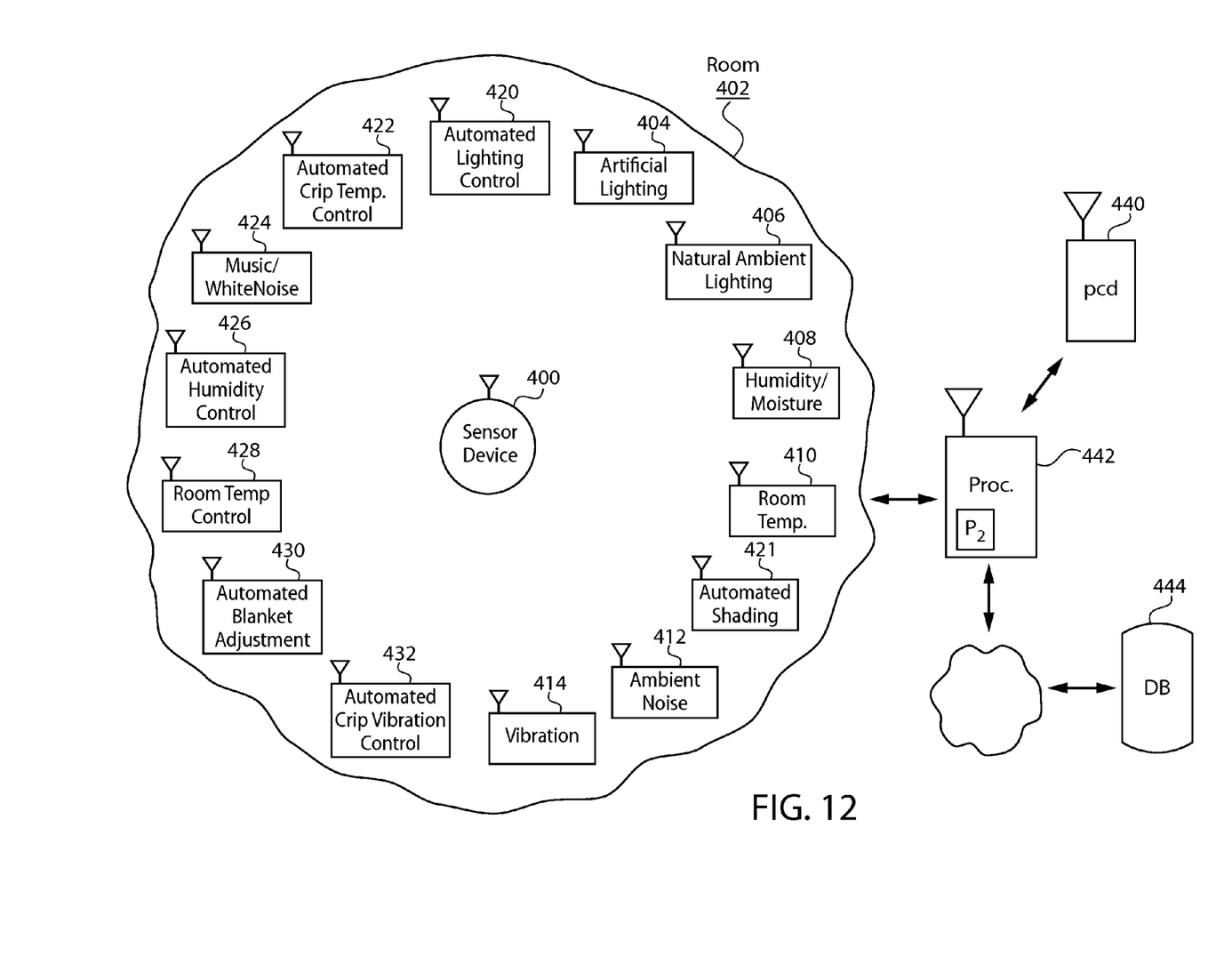
FIG. 12 shows an illustrative diagrammatic view of a monitoring system in an infant or child's room in accordance with a further embodiment of the present invention.

As shown in FIG. 12, many devices (of a variety of manufacturers) may be combined with a system of the invention to provide not only information regarding breathing, but a wide variety of sets of data and control. For example, a motion device 400 may be used in a room 402 that also includes wirelessly connected artificial lighting sensors 404, natural light sensors 406 (that sense outside of the visible spectrum), humidity I moisture sensors 408, room temperature sensors 410, ambient noise sensors 412 and room or crib vibration sensors 414. Knowing this data, caregivers may in turn be permitted to control aspects of the room, such as by using an automated lighting control unit 420, an automated shading control unit 421, an automated crib temperature control unit 422, a music I white noise generator 424, an automated humidity control unit 426, a room temperature control unit 428, an automated blanket adjustment system 430 (such as to affect heat or movement of a blanket), and/or an automated crib vibration or swing control system 432. The communication to and from the personal communication device 440 via the base station 442 may be as discussed above. The base station 442 may also communicate via a further wireless network (such as the Internet) to a database 444.

Figure 13:
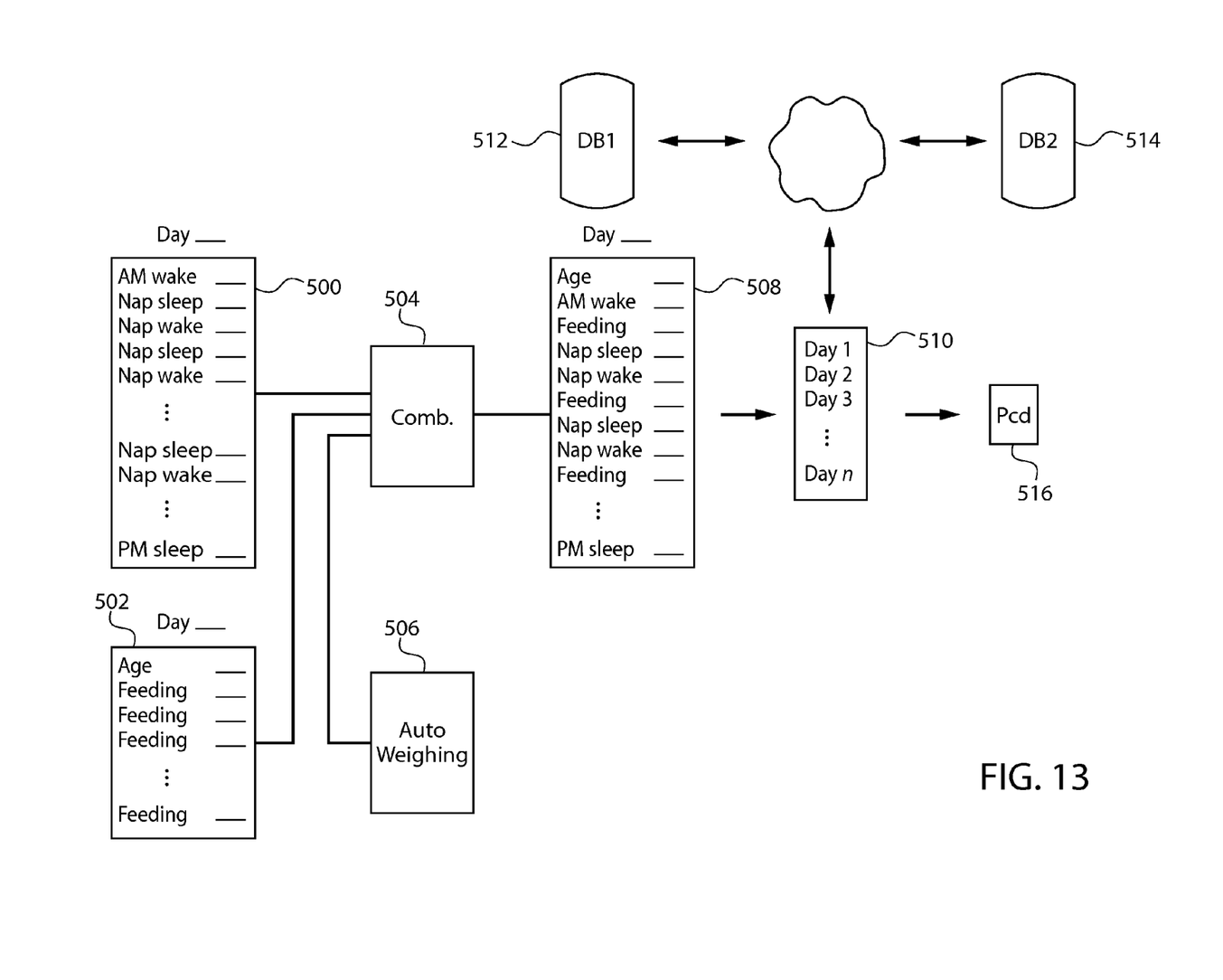
FIG. 13 shows an illustrative diagrammatic view of an analytics compilation and analysis system in accordance with an embodiment of the present invention.

With reference to FIG. 13, a system in accordance with an embodiment of the invention may provide a sensed data report 500 that includes data regarding the timing of waking, napping and falling asleep for the night for each day over a period of time. The system may also permit a caregiver to enter data to provide input data 502 regarding, for example, feeding times. The processor includes a combiner module 504 that generates a combined report 508 for each day. In certain embodiments, an automated weighing station 506 may provide information regarding the amount of food (e.g., in ounces) was consumed at each feeding. A combined report 508 is then provided for each day, and a period report (e.g., monthly) 510 is generated for analysis purposes. The system may compare either the combined report 508 or the period report 510 with other reports for the same child for prior periods in time (via a database 512) or may compare the combined report 508 or the period report 510 with such reports of other children via a database 514. Comparison output reports may then be provided to the personal communication device 516 of the caregiver.

Figure 14A:
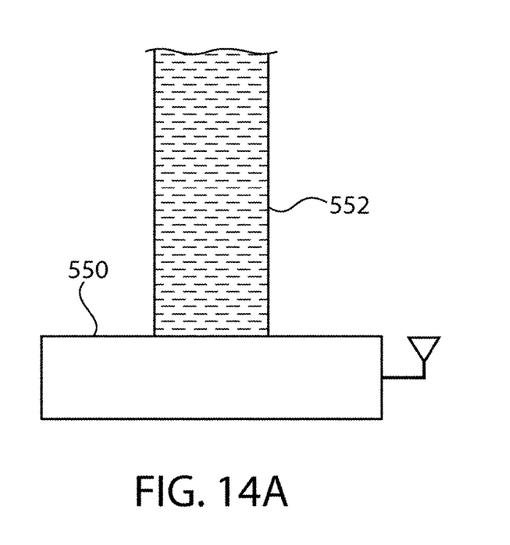
FIGS. 14A and 14B show illustrative diagrammatic views of an automated weighing system for use in accordance with an embodiment of the present invention.
Figure 14B:
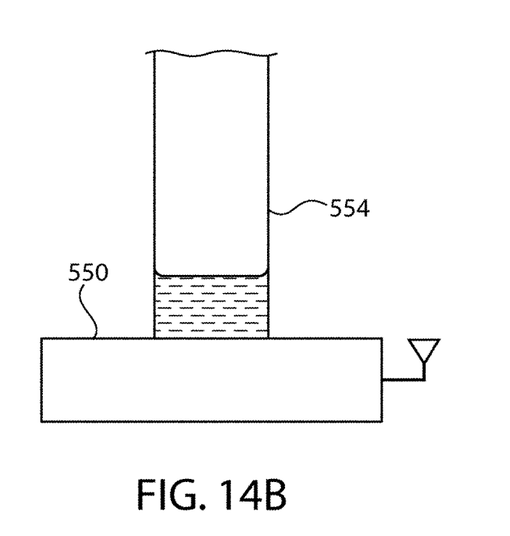
Figure 15A:
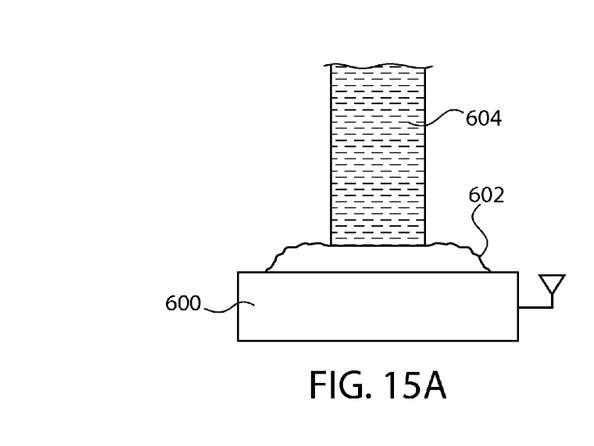
FIGS. 15A-15D show illustrative diagrammatic views of another automated weighing system for use in accordance with an embodiment of the present invention.
Figure 15B:
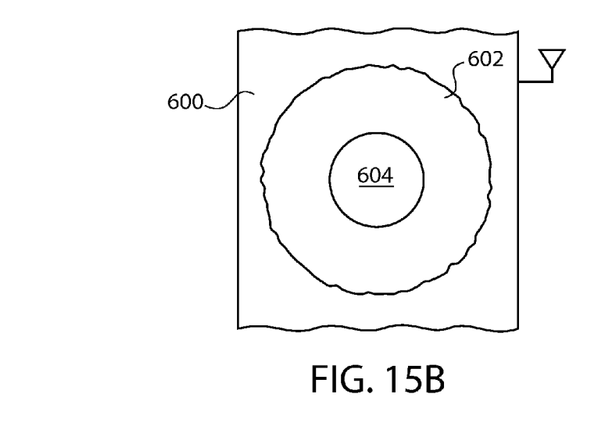
Figure 15C:
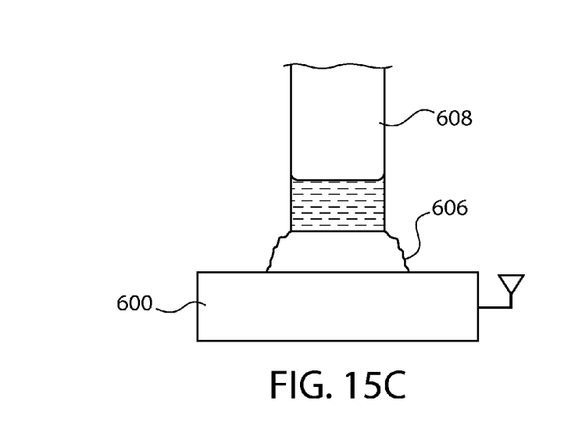
Figure 15D:
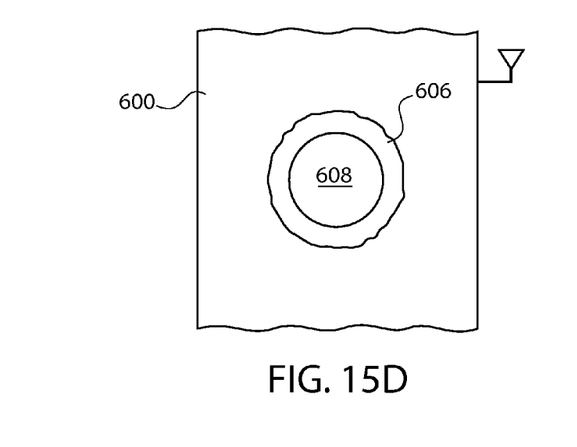

With reference to FIGS. 14A and 14B, an automated weighing station for use with a system in accordance with an embodiment of the present invention may include a scale 550 that is wirelessly connected to the network, and that may provide a weight measurement difference between a full feeding bottle 552 (prior to feeding), an a finished feeding bottle 554 (following feeding). This difference in weight may be added to the combiner 504 of FIG. 13 to provide additional timed, volumetric data regarding each feeding.

With reference to FIGS. 15A-15D, another automated weighing station for use with a system in accordance with another embodiment of the invention may employ a weighing application that senses a widening of a spread of a material under the weight of a bottle. For example, a screen of a person communication device 600 may be used to determine the spread of an elastic substance 602 (such as a low-durometer thermoplastic compound) under the weight of a full feeding bottle 604 versus the spread of the same substance (as shown at 606 under the lesser weight of a finished feeding bottle 608. The substance has a similar size and capacitive characteristic to a human finger, allowing the screen of a tablet device to detect positioning and therefore determine weight. In accordance with a further embodiment, the substance may be formed in a spider-like shape, allowing the legs to spread out responsive to the weight of the item being weighed. Again, the time stamped information may be provided wirelessly to the system shown in FIG. 13.

Figure 16:
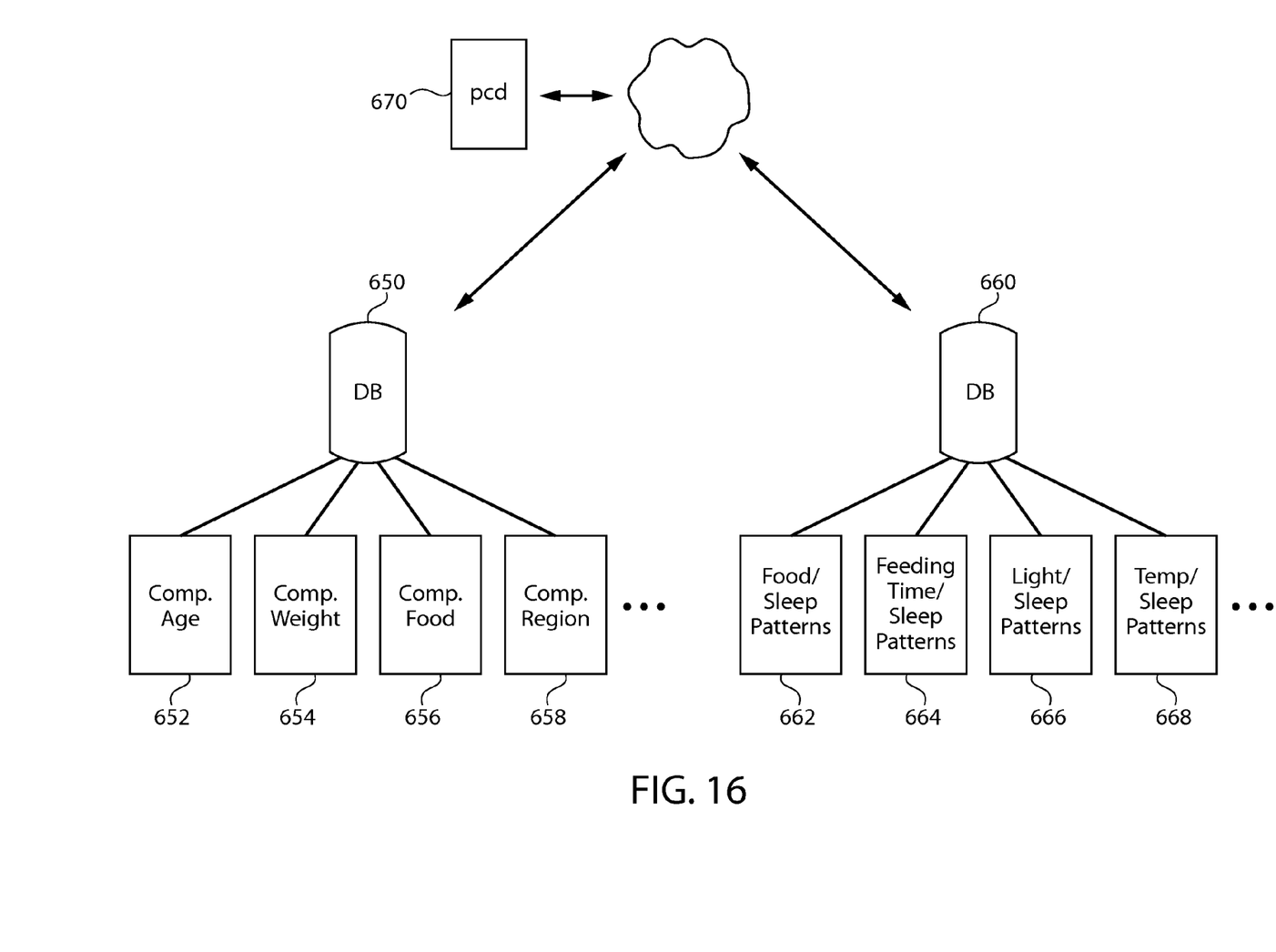
FIG. 16 shows an illustrative diagrammatic view of a data analytics system In accordance with an embodiment of the present invention.

With reference to FIG. 16, a system in accordance with a further embodiment of the invention may communicate (again, e.g., via a network such as the Internet) with various databases that include collected data for many subjects. For example, the database 650 may provide comparisons to a caregiver comparing the infant under that person's care with data collected regarding infants of a similar age (report at 652), infants regarding a similar weight (report at 654), infants regarding a similar diet (report at 656), and infants from the same or a similar geographic region (report at 658). The database 660 may provide pattern analyses for a particular infant under the caregiver's care regarding patterns of diet and sleep times (report at 662), feeding times and sleep times (report at 664), light patterns and associated sleep patterns (report at 666) and temperature patterns and associated sleep patterns (report at 668). All of this information may be provided to the caregiver comparing the infant under their care to a wide variety of data regarding other children as well as patterns of activities in the infant's own life that may be affecting sleep patterns.

The system may also employ machine learning algorithms to derive new correlations and analyses, having gathered a large amount of data from a large number of infants, toddlers, children etc.

While the foregoing has been with reference to particular embodiments of the invention, it will be appreciated by those skilled in the art that changes in the above disclosed embodiments may be made without departing from the principles and spirit of the disclosure, the scope of which is defined by the appended claims.

What is claimed is:

1. A system for monitoring a status of a subject, said system comprising:

a first processor coupled to a motion sensor that is positionable adjacent a torso of the subject, said first processor configured to continuously determine, via the motion sensor, if no change in motion of the subject is detected for a predetermined period of time, the predetermined period of time being one second; and a second processor in communication with the first processor, said second processor configured to receive an alert signal from the first processor, the alert signal being configured to be sent by the first processor when the no change in motion of the subject is detected by the motion sensor for the predetermined period of time.

2. The system as claimed in claim 1, wherein said second processor sends polling requests to the first processor regarding any of status, temperature or battery power of a device that includes the first processor and the motion sensor.

3. The system as claimed in claim 1, wherein the alert signal from said first processor comprises an interrupt request to the second processor when the no change in motion of the subject is detected by the motion sensor for the predetermined period of time.

4. The system as claimed in claim 1, wherein the motion sensor is not in a fixed position with respect to the torso, but is permitted a range of movement with respect to the torso.

* * * * *